United States Patent
Reinmuller

[11] Patent Number: 5,731,298
[45] Date of Patent: Mar. 24, 1998

[54] METHOD FOR THE TREATMENT OF SCARS AND KELOIDS

[76] Inventor: Johannes Reinmuller, Gustav-Freytag-Strasse 27, 65189 Wiesbaden, Germany

[21] Appl. No.: 256,040

[22] PCT Filed: Dec. 24, 1992

[86] PCT No.: PCT/EP92/02990

§ 371 Date: Aug. 15, 1994

§ 102(e) Date: Aug. 15, 1994

[87] PCT Pub. No.: WO93/12801

PCT Pub. Date: Jul. 8, 1993

[30] Foreign Application Priority Data

Jan. 3, 1992 [DE] Germany .................... 42 00 080.7

[51] Int. Cl.$^6$ .................... A61K 31/715; C08B 37/00
[52] U.S. Cl. .................... 514/54; 514/55; 514/56; 514/62; 536/53; 536/20; 536/21; 536/55.2; 536/123.1
[58] Field of Search .................... 514/54, 55, 56, 514/62; 536/20, 21, 55.2, 53, 123.1

[56] References Cited

U.S. PATENT DOCUMENTS

| | | | |
|---|---|---|---|
| 4,350,629 | 9/1982 | Yannas et al. | 530/356 |
| 4,582,865 | 4/1986 | Balazs et al. | 524/29 |
| 4,613,502 | 9/1986 | Turková et al. | 424/94.3 |
| 4,863,907 | 9/1989 | Sakurai et al. | 514/56 |
| 4,947,840 | 8/1990 | Yannas et al. | 602/50 |
| 5,093,319 | 3/1992 | Higham et al. | 514/55 |

FOREIGN PATENT DOCUMENTS

| | | |
|---|---|---|
| 2129300 | 5/1984 | United Kingdom . |
| 89/04172 | 5/1989 | WIPO . |

OTHER PUBLICATIONS

Yannas et al. *J. Biomed. Mater. Res.* 1980, 14, 65–81. month not available.

Friderich *Z. Allgemeinemedizin* 1985, 61, 1101–1103. month not available.

Dockery et al. *Clinics Podiatric Med. Surg.* 1986 3(3), 473–485. month not available.

Nicolai et al. *Aesth. Plast. Surg.* 1987, 11, 29–32. month not available.

Davidson et al. *Clin. Mater.* 1991, 8, 171–177. month not available.

Biagini et al. *Biomaterials* 1991, 12, 281–286. month not available.

Sorrone et al. *Riv. Ital. Chir. Plastica* 1986, 18, 205–207. month not available.

Primary Examiner—Kathleen K. Fonda
Attorney, Agent, or Firm—Felfe & Lynch

[57] ABSTRACT

A method and a pharmaceutical composition for non-topical wound, scar and keloid treatment is described which contains cross-linked glycosaminoglycans and conventional pharmaceutical auxiliary and/or carrier substances. The pharmaceutical composition is preferably administered intralesionally e.g. by injection in the form of a gel containing water. The cross-linked glycosaminoglycans are also suitable for use as cosmetics and skin care products.

3 Claims, No Drawings

METHOD FOR THE TREATMENT OF SCARS AND KELOIDS

This is in an application under 35 U.S.C. §371 of PCT/EP92/02990 having an international filing date of Dec. 24, 1992.

BACKGROUND OF THE INVENTION

The invention concerns a pharmaceutical composition for the treatment of wounds, scars and keloids.

Excess new growth of scar tissue occurs in many people during healing of skin wounds. In medical terminology this new formation of tissue is referred to as cicatricial hypertrophy or as keloid in severe cases. These are unpredictable reactions during wound healing caused by a predisposition. Up to now the reasons for excess cicatrisation are not known. Thus at present there is also no scientifically based causal method of treatment.

Numerous methods have been described for keloid treatment (cf. e.g. McCarthy/Convers "Plastic Surgery", volume 1, pages 732–747, W. B. Saunders, 1990). However, they are all more or less empirically based and do not have a secure foundation in a strict scientific sense. This is due on the one hand to a lack of basic knowledge and is also due to the fact that a spontaneous tendency of untreated keloids to regress is often observed.

As a consequence there is an extremely large number of competing methods of treatment whose effectiveness is, however, doubtful and of which the most important are briefly described in the following.

It is necessary to differentiate between mechanical (physical) and medicinal (chemical) methods of treatment.

The mechanical methods of treatment encompass the application of pressure on the keloid by external compression bandages and the application of foils made of silicon elastomers. A major disadvantage in this case is that the application has to be carried out over months and years. It can also not be used to the same extent in all body regions; thus for example an adequate degree of compression cannot be achieved on the neck. In addition extensive compression bandages always mean a considerable restriction in the freedom of movement and quality of life for the carrier. Moreover they also create considerable problems of hygiene, in particular in the warm period of the year and in hot countries. Compression bandages can also again lead to renewed tissue lesions by the mechanical strain on the sensitive scar skin and thus again promote keloid formation.

The physical methods also include cold treatment (cryotherapy) and laser therapy. Both methods produce tissue necroses by cold or heat by which means the active connective tissue cells and the fibrous substance within the keloid are destroyed. The keloids temporarily collapse and tissue defects are formed. During the subsequent healing of these defects, connective tissue cells again immigrate by which means the formation of keloid starts again. Consequently this method of treatment can thus always only achieve short-term improvements but no final healing.

In the case of the medicinal methods it is necessary to differentiate between preparations for external application and for injection.

In the case of the agents for external application, these are usually ointments with a great variety of active substances such as e.g. hormones, amino acids, mucopolysaccharides. Plant extracts such as from the thorn-apple are also used. A preferred component of preparations for the external treatment of scars and cicatricial keloids is heparin (cf. e.g. "Pharmazie in unserer Zeit" 10 (1981), page 168 to 181).

All preparations of active substances for external applications have the same inherent disadvantage, namely that the external application, i.e. spreading on the skin over the keloid, does not ensure an adequate tissue concentration in the keloid itself which can reach a thickness of up to several centimetres. Due to the excessively increased blood circulation within the keloids, the active substances—provided that they can penetrate the skin barriers at all—are rapidly transported away via the blood and lymph stream. The diffusion of the active substances in the tissue therefore only plays a subordinate role in the distribution.

It is also known that the active substance heparin cannot penetrate the epidermal layers. Thus the effect of externally applied preparations, such as e.g. ointments based on heparin, on connective tissue cells is doubtful. It cannot therefore be excluded that the successes achieved with scar ointments containing heparin could be ascribed to spontaneous healing.

Derivatives of the hormone cortisol (hydrocortisone) are used in the invasive methods of treatment for keloids; due to the known increased blood circulation within keloids and the concomitant rapid transport of pharmaceutical agents, the crystalline poorly soluble forms are preferably used with which a depot effect can be achieved. Since cortisol and its derivatives strongly inhibit the cells of connective tissue, the quantitatively and qualitatively strongest changes in keloids can be achieved at present with the invasive administration (injection) of pharmaceutical preparations based on crystalline corticoids (corticosteroids).

However, a decisive disadvantage of this therapy with corticoids is the lack of control of the reaction. Therefore in the practical application this can either result in an undesired scar atrophy i.e. a divergence and sinking of the scar with corresponding disfigurement or in an inadequate reaction of the tissue with an unsatisfactory therapeutic result.

A further disadvantage of corticoid therapy is the systemic action of the dissolved active substance which prevents its use in the case of keloids of large area or in children.

SUMMARY OF THE INVENTION

The object of the invention is to provide a pharmaceutical composition for the treatment of wounds, scars and keloids with which the aforementioned disadvantages that occur in previous methods of treatment can be avoided, in particular the undesired side-effects of corticoid therapy such as e.g. local over-reactions, that can be administered easily and successfully and is degraded by the organism.

This object is achieved by the pharmaceutical composition of the invention which contains cross-linked glycosaminoglycans and conventional pharmaceutical auxiliary and/or carrier substances.

Practical embodiments thereof are the subject matter of this invention.

A further subject matter is also a process for the production of the pharmaceutical compositions according to the invention.

It is possible using the compositions according to the invention to avoid the undesired properties of corticoid therapy. Namely it was found that the cross-linked glycosaminoglycans (GAG, mucopolysaccharides) used according to the invention have an inhibitory effect on keloid formation when they are administered non-topically (intralesionally). In this case no local over-reactions occur as is the case with the corticoids and also no systemic effects. A further advantage is the biological degradability in the organism.

Moreover the compositions according to the invention also allow the successful treatment of deep scar formations in connective tissue such as e.g. Dupuytren's disease of the palmar surfaces or the so-called Induratio penis plastica (IPP) which form without prior injury (cross-section).

DETAILED DESCRIPTION OF THE INVENTION

Cross-linked glycosaminoglycans according to the invention are understood to be those in which two or several of the same and/or different glycosaminoglycans are linked together to form a molecular unit. The cross-linking is preferably carried out by chelate formation, complex formation and/or salt formation and in particular by a chemical cross-linking.

Natural or synthetic glycosaminoglycans and also substances that are chemically related thereto can be used as glycosaminoglycans. They can be of an anionic or cationic character.

Natural glycosaminoglycans that are preferably used are those that occur in human connective tissue in particular e.g. hyaluronic acid, heparin, heparin sulfate, chondroitin sulfate. Sulfated polysaccharides are preferably used as synthetic glycosaminoglycans. Substances that are chemically related to glycosaminoclycans that are used according to the invention are preferably those of biological origin and in particular chitosamine and chitosan or their derivatives such as e.g. N-carboxybutlychitosan (cf. R. Muzzarelli et al., Carbohydrate Polymers 11 (1989) 307-320). The formation of chelates, poorly soluble salts or complexes of glycosaminoglycans which also represent a cross-linking within the sense of the invention is achieved by a holding-together through ionic forces as is common for such chelates, salts or complexes.

The cross-linked glycosaminoglycans used according to the invention can be produced in a well-known manner. The chemical cross-linking in this process is usually carried out by cross-linking with bifunctional reactive agents such as e.g. glutaraldehyde or carbodiimide; it is, however, also for example possible to produce cross-linking via amide bonds by means of bifunctional amino acids such as lysine, protamines or albumins. If glycosaminoglycans or analogues thereof that have been produced synthetically are used according to the invention then these can already be primarily cross-linked during production so that a further treatment for cross-linking is not necessary. Such glycosaminoglycans are partly commercially available already in a cross-linked state and can be used directly according to the invention (e.g. "Hylon" and "Hylagel", a cross-linked hyaluronic acid from the Biomatrix Company NJ, USA; for the production c.f. also U.S. Pat. Nos. 4,713,448, 4,605,691).

It is preferable to cross-link identical glycosaminoglycans are preferably and then use them according to the invention but it is also possible according to the invention to use a combination of two or more different or partially different glycosaminoglycans. In a particularly preferred embodiment, glycosaminoglycans with an extremely long chain (molecular weight preferably between 100,000 and 1,000,000) are used; in this case the degree of cross-linking can then remain low. The products are practically free of protein.

In a particularly preferred embodiment of the invention intermolecularly cross-linked heparin is used as the cross-linked glycosaminoglycan.

The intermolecular cross-linking of heparin can for example be carried out in the following manner: commercially available heparin is treated with dilute nitric acid by which means reactive aldehyde groups are formed on the heparin; subsequently a reductive animation is carried out by means of $NaBH_3CN$. Covalent bonds are formed between the individual heparin chains (end and side chains) via the free amino functional groups of heparin.

A cross-linking of heparin by complex formation is preferably carried out with protamines, gentamycin or vancomycin, metal ions such as e.g. $Fe^{2+}$, $Zn^{2+}$.

The pharmaceutical compositions according to the invention contain the cross-linked glycosaminoglycans preferably in amounts of 0.1 to 20% by weight in relation to the total pharmaceutical composition and in particular in an amount of 0.5 to 10% by weight and especially preferably in an amount of 1 to 5% by weight.

The pharmaceutical compositions according to the invention can be present in the form of preparations that can be administered intralesionally and in particular in the form of injectable gels preferably with a water content of 80 to 99% by weight and also as an anhydrous precursor e.g. lyophilized powder in the form of a powder. The pharmaceutical auxiliary and carrier substances that can be used are those that are conventionally used for this purpose and are suitable for the application according to the invention and are compatible with the cross-linked glycosaminoglycans. The preferred carrier substance is water.

The pharmaceutical compositions according to the invention can for example contain agents to set the pH value, stabilizers, antioxidants, solubilizers, agents that promote penetration, preservatives and/or gel formers as pharmaceutical auxiliary substances as they are usually used in such compositions. They are used in the usual amounts for such preparations.

The pharmaceutical compositions according to the invention can in addition to the actual active substances (cross-linked glycosaminoglycans) also contain further pharmaceutically active substances that are compatible with the cross-linked glycosaminoglycans within the scope of the application e.g. active substances for the therapy of skin diseases (dermatoses), antibiotics (in particular antibiotics with a charge of opposite polarity such as e.g. gentamycin and vancomycin with a positive charge for e.g. cross-linked heparin, or e.g. penicillins or cephalosporins with a negative charge for e.g. cross-linked chitosamine), sulfonamides, disinfectants, hormones (e.g. corticoids) and hormone derivatives (e.g. cortisol), local anaesthetics e.g. of the lidocaine or novocaine type, vasoactive substances for vascular constriction (avoidance of bleeding), adrenalin, enzymes such as e.g. hyaluronidase, interleukins, growth factors e.g. EGF, PDGF and/or IGF, skin care agents and/or agents that stimulate blood flow (hyperaemising agents). These substances can be present bound firmly to the glycosaminoglycans such as e.g. antibiotics with a heteropolar charge of opposite polarity i.e. as a component of the cross-linked glycosaminoglycans and are then released during the degradation of the cross-linked glycosaminoglycans or they can be released by a controlled release type of system.

In the preferred application according to the invention in the form of an injection, the preparations can for example contain local anaesthetics to avoid pain when the injection cannula is inserted. The preparations preferably contain an anionically or cationically charged molecule such as gentamycin as an antibiotic which is bound as a counter-ion to the cross-linked glycosaminoglycans and thus remains immobilized in loco which prolongs the action accordingly.

The compositions according to the invention can be produced in a conventional, generally known manner for the production of such compositions. In this process the order of mixing of the individual components is usually not critical.

The invention also concerns a process for the production of the compositions which is characterized in that the cross-linked glycosaminoglycan and the other components are dissolved in the pharmaceutical carrier. Water is preferably used as the pharmaceutical carrier and it is expedient to carry out the process while heating and subsequently cooling. For protection against oxidation it may be expedient to work under an inert gas atmosphere in particular under nitrogen.

The type, dose and frequency with which the composition according to the invention is administered depends in particular on the severity of the disease and the general state of the patient and also quite generally on the state and the sensitivity of the skin scar. If the compositions according to the invention are administered in the form of preparations that can be applied topically then the administration is as a rule in accordance with the usual conditions for such compositions.

The type of treatment and frequency of administration also depends in particular on the individual response of the person to be treated. An application of gels is preferably carried out at intervals of 1 to 2 months.

If the compositions according to the invention in the form of injectable gels are applied intralesionally which is primarily the case then this is preferably carried out by injection with the aid of fine cannulae and with pressure-resistant syringes. The gels according to the invention can also be shot percutaneously with the aid of compressed air instruments; compressed air instruments such as those that are known in medicine for such an application can be used for this.

In a particularly preferred embodiment of the invention the pharmaceutical preparation in the form of an injectable gel contains cross-linked heparin as the cross-linked glycosaminoglycan. Whereas for example the injection of non-cross-linked heparin does not come into consideration because heparin inhibits blood coagulation and is additionally rapidly transported out of the lesion via the vascular system and then has a systemic effect similar to the corticoids, heparin loses its inhibitory properties on blood coagulation in the cross-linked form according to the invention and cannot be transported away via the blood and lymph stream. It therefore remains active at the site of application in the keloid tissue for weeks and months after injection. Degradation is primarily via phagocytosis by special cell populations.

When the compositions according to the invention are used which contain cross-linked glycosaminoglycans there is also no occurrence of local over-reactions and no systemic effects such as is the case for corticoids. A further advantage is the biological degradability in the organism. Thus for example the intralesional application by injection can be repeated at intervals of 4 to 8 weeks.

An advantage of the preferred preparations according to the invention in the form of injectable gels and their intralesional application is also that no additional hygienic measures whatsoever are necessary after the injection sites have healed. All regions of the body can be treated in the same manner and the mobility of the patients is not restricted by bandages. Treatment with the preparations according to the invention can also prevent an occurrence or reoccurrence of keloids which demonstrates its preventive effect.

The invention therefore also concerns the use of cross-linked glycosaminoglycans for the treatment of wounds, scars and primarily keloids and for the production of a pharmaceutical composition for wound, scar and keloid treatment. In this case the aforementioned glycosaminoclycans that were stated as being preferred are preferably used as the cross-linked glycosaminoglycan.

A particular method of application for the prevention of keloids or contract scars is the administration of anhydrous precursors of cross-linked glycosaminoglycans (e.g. as a lyophilisate) in the form of a wound powder into fresh wounds. In this case the powder is sprinkled into the open wound or wound cavity before wound closure. The wound is then closed by a suture, clamps etc.. In the wound the powder takes up water from the tissue and then corresponds to the preparation according to the invention in the form of a gel or itself represents a preparation according to the invention.

The powder or gel form can also be introduced into large body cavities to prevent undesired adhesions e.g. into the abdominal cavity or thoracic cavity during a surgical operation on the intestine or the lung, into the pericardium, or after operative procedures via indwelling drainages. In the case of inflammatory effusions into large body cavities, the preparation according to the invention can also be introduced via the indwelling cannula after puncturing and emptying the effusion.

The preparation according to the invention which may be on a suitable carrier (e.g. tampon) can also be introduced into cavities and ducts of the body that are accessible from the outside e.g. into the main nasal cavities and paranasal sinuses or into the meati of the nose or into the tear ducts to prevent scarred adhesions.

It is known from U.S. Pat. No. 4,605,691 that cross-linked gels of hyaluronic acid can be use alone or together with other hydrophilic polymers in cosmetic formulations. R. Muzzarelli et al. (1.c) also describe the use of N-carboxybutylchitosan for cosmetic preparations.

It was now surprisingly found that the cross-linked glycosaminoglycans according to the invention that are described above are excellently suitable as a carrier or component of cosmetics and skin care products.

The present invention therefore also concerns the use of the cross-linked glycosaminoglycans described above with the exception of cross-linked hyaluronic acid or cross-linked N-carboxybutylchitosan for cosmetics or as skin care products. In particular the cross-linked glycosaminoglycans that were previously stated as being preferred and distinctively described are used for this.

The cosmetic preparations and skin care products can be present in the usual forms for such preparations e.g. as creams, ointments, lotions and in particular as gels that can be applied topically. They can also contain other auxiliary and/or carrier substances that are conventionally used for this that are compatible with the cross-linked glycosaminoglycans according to the invention. In addition they can also contain the auxiliary substances and/or further active substances described previously in connection with the pharmaceutical preparations, provided that they are compatible with the cross-linked glycosaminoglycans within the scope of the application and are practical.

It is intended to elucidate the invention in more detail by the following examples without limiting it thereto.

EXAMPLE 1

Production of an injectable gel from the following components:

| Component | Amount |
| --- | --- |
| cross-linked hyaluronic acid ("Hylagel" Biomatrix Co., NJ, USA) | 0.004 g |
| lidocaine hydrochloride | 0.02 g |
| water, purified (DAB 9) | to 1.0 g |

The components are dissolved under a nitrogen atmosphere while stirring and briefly heating; a colourless clear gel is obtained after cooling; pH value: 7.00±0.1.

The gel is dispensed into pressure-resistant piercable ampoules and sealed. Afterwards a heat sterilization is carried out and the gel is stored protected from light.

Application example 1

The treatment of a ca. 3 cm×5 cm dark-red raised keloid is described which was present on the back of a 30 year old woman after a tangential cut by a broken pane of glass.

The patient complained about itching in the area of the keloid. The keloid was infiltrated with cross-linked hyaluronic acid (Hylon) by injection for a total of four times at intervals of 4 to 8 weeks. The itching had already disappeared a few hours after the first injection. The keloid became considerably paler within two weeks and a flattening was already recognizable after four weeks. After ca. 6 months there was a pale, only slightly raised scar.

Application example 2

The treatment of a keloid in the lower fold of the breast (right and left) is described which occurred in a female patient after surgical breast correction.

The keloids were treated several times using conservative methods (topical preparations) and repeatedly excised. After the last excision, cross-linked hyaluronic acid was injected during the operation into the wound edges on the right side. Then both sides were sutured identically. The sutures were removed on the right and left side after two weeks. After four weeks the untreated scar on the left side was raised considerably more and was more reddened than the scar on the right side treated with hyaluronic acid. In addition it was possible to successfully prevent the reoccurrence of a keloid on the right-hand side. This also demonstrates the preventive effect of the pharmaceutical preparation according to the invention.

I claim:

1. A method for treating a pre-existing scar or pre-existing keloid comprising injecting a composition comprising a pharmaceutically effective amount of a cress-linked hyaluronic acid in combination with a pharmaceutically acceptable carrier into the pre-existing scar or pre-existing keloid, wherein the pharmaceutically effective amount of a cross-linked hyaluronic acid is 0.1% to 20% by weight of the composition.

2. A method for treating a scar or keloid according to claim 1, wherein said cross-linked hyaluronic is cross-linked by chemical cross-linking, chelate formation, complex formation or salt formation.

3. A method for treating a scar or keloid according to claim 1, wherein said cross-linked hyaluronic acid is cross-linked by chemical cross-linking.

* * * * *